United States Patent [19]

Van Horn

[11] Patent Number: 5,079,238

[45] Date of Patent: Jan. 7, 1992

[54] STABILIZED O-HALOPYRIDYLPHOSPHATE COMPOSITIONS AND METHOD OF USE

[75] Inventor: Roy L. Van Horn, Beaverton, Mich.

[73] Assignee: DowElanco, Indianapolis, Ind.

[21] Appl. No.: 380,922

[22] Filed: Jul. 17, 1989

Related U.S. Application Data

[63] Continuation-in-part of Ser. No. 176,543, Apr. 1, 1988, abandoned, which is a continuation-in-part of Ser. No. 15,769, Feb. 17, 1981, abandoned.

[51] Int. Cl.$^5$ .......................... A01N 51/16; C07F 9/16
[52] U.S. Cl. ........................ 514/89; 514/919; 514/920; 546/25; 558/71
[58] Field of Search ............... 514/89, 920; 546/25; 558/71

[56] References Cited

U.S. PATENT DOCUMENTS

| | | | |
|---|---|---|---|
| 3,244,586 | 4/1966 | Rigterink | 167/33 |
| 4,196,293 | 4/1980 | Pawlowski | 546/25 |
| 4,223,025 | 9/1980 | Rigternik | 546/25 |
| 4,224,318 | 9/1980 | Pawlowski | 546/25 |
| 4,361,155 | 11/1981 | Larson | 514/89 |
| 4,380,537 | 4/1983 | Monroe | 424/200 |
| 4,631,301 | 12/1986 | Rozuma et al. | 514/89 |
| 4,665,061 | 5/1987 | Reibel et al. | 546/25 |
| 4,678,776 | 7/1987 | Maurer et al. | 514/89 |
| 4,777,164 | 10/1988 | DeVries et al. | 514/89 |

FOREIGN PATENT DOCUMENTS 0185778  7/1986  European Pat. Off. ............ 514/89

OTHER PUBLICATIONS

All references are found in patent application Ser. No. 07/015,769.

*Primary Examiner*—Mukund J. Shah
*Assistant Examiner*—Jyothsna Venkat
*Attorney, Agent, or Firm*—S. Preston Jones; Ronald G. Brookens

[57] ABSTRACT

Insecticide compositions containing an O-halopyridylphosphate insecticide absorbed on corn flour or a mineral carrier are stabilized from thermal decomposition by incorporating from about 1 to about 20 percent by weight of the carrier of a wood flour or a hemicellulose extract. These compositions can be employed in methods for protecting stored grains and plants from insect damage.

22 Claims, No Drawings

STABILIZED O-HALOPYRIDYLPHOSPHATE COMPOSITIONS AND METHOD OF USE

CROSS-REFERENCE TO RELATED APPLICATION

The present application is a continuation-in-part of application Ser. No. 176,543, filed Apr. 1, 1988 now abandoned which in turn is a continuation-in-part of application Ser. No. 015,769, filed Feb. 17, 1987, now abandoned.

BACKGROUND OF THE INVENTION

The present invention relates to a method for stabilizing O-halopyridylphosphate insecticide-carrier admixtures and to the novel stabilized insecticide compositions.

SUMMARY OF THE INVENTION

The present invention is directed to a composition comprising:
(a) an insecticidally-effective amount of an O-halopyridylphosphate insecticide of the formula:

$$R-O-\overset{Z}{\underset{\underset{OCH_3}{|}}{P}}\diagup OCH_3$$

wherein R represents halopyridyl and Z represents oxygen or sulfur, in admixture with
(b) an inert carrier which is a corn flour or a mineral clay from the group consisting of diatomaceous earth and kaolinite clays, or a mixture of said carriers and
(c) an amount of an inert stabilizing material effective to thermally stabilize the insecticide-carrier mixture, said stabilizing material is a wood flour or a hemicellulose extract or a mixture thereof.

Preferably, the stabilizing material is a wood flour, and most preferably the wood flour is a softwood flour.

In the present invention, the wood flour and hemicellulose extract are employed in the compositions in an amount effective to thermally stabilize the insecticide-carrier admixture.

The present invention is also directed to a method for protecting stored grains and plants from insect damage by treating stored grain and/or plants with said compositions.

DETAILED DESCRIPTION OF THE EMBODIMENTS

For the purposes of this application, the terms "dusts", whether high or low concentrate, and "compositions" are used interchangeably and have the same meaning.

The O-halopyridylphosphate insecticides employed in the compositions of the present invention are of the formula:

$$R-O-\overset{Z}{\underset{\underset{OCH_3}{|}}{P}}\diagup OCH_3$$

wherein R represents halopyridyl and Z represents oxygen or sulfur.

The O-halopyridylphosphates employed in the compositions of the present invention and the methods for their preparation are disclosed in U.S. Pat. No. 3,244,586. The teachings of this patent related thereto are incorporated herein by reference.

The term "chlorpyrifos-methyl" as employed in the present specification and claims is the common name of the compound otherwise known as O,O-dimethyl O-3,5,6-trichloro-2-pyridyl)phosphorothioate and is represented by the formula:

$$\text{(structure: 3,5,6-trichloro-2-pyridyl O,O-dimethyl phosphorothioate)}$$

The O-halopyridylphosphate insecticide is normally admixed with the desired carrier (corn flour and/or mineral clay) and the stabilizing material to make either high or low concentrate dusts. Low concentrate dusts are those which can be directly applied to control unwanted pests, i.e., those in stored grain or in storage facilities such as silos, storage bins, and the like. High concentrate dusts are usually diluted with additional carrier prior to use. The concentration of the O-halopyridylphosphate in high concentrate dusts can range from about 10 to about 95 percent (weight basis) or more, preferably from about 30 to about 90 percent, more preferably between about 30 and about 50 percent by weight insecticide. The concentrations of the O-halopyridylphosphate insecticide in low-concentrate dusts can range from about 0.1 to about 10 percent (weight basis), preferably from about 1 to about 5 percent, most preferably from about 2 to about 3 percent by weight.

The term "wood flour" as used herein designates pulverized hardwoods or softwoods or mixtures thereof. The particle size of the wood flour can range from about 2 to about 2400 microns.

The term "softwood flour" as used herein designates pulverized dried wood flour derived from softwood wastes or from softwood manufacturing processes. A source of softwood flour can be obtained as Wilner wood flour #2501 from the Wilner Wood Products Company, Norway, Maine.

The term "hardwood flour" as used herein designates pulverized dried wood flour derived from hardwood wastes or from hardwood manufacturing processes. A source of hardwood flour can be obtained as Wilner wood flour #247, from the Wilner Wood Products Company.

The term "hemicellulose extract" refers to the extract obtained by extracting water-soluble hemicelluloses from the liquid stream of wood pulp using steam and pressure. The extracted solution of hemicelluloses is evaporated to a standard solids content of about 57 percent and is largely free of lignin. A source of hemicellulose can be obtained as Masonex ®, trademark of the Masonite Corporation, Chicago, Ill.

The term "corn flour" as used herein designates dried corn kernels ground to a particle size of from about 2 to about 2400 microns.

The term "Diatomaceous Earth" designates a soft, bulky solid material (about 88 percent or more silica) composed of skeletons of small prehistoric aquatic plants related to algae (diatoms). A source of diatomaceous earth is Celite ® 209, trademark of the Johnsons-Manville Products Corporation, Celite Division, Manville, N.J.

The term "Barden Clay" defines a kaolinite clay having an average chemical analysis of about 45 percent silicon dioxide ($SiO_2$) and 38 percent aluminum oxide ($Al_2O_3$). Barden clay is produced from a deposit of sedimentary kaolinite near Graniteville, S.C., and can be obtained from the J. M. Huber Corporation, New York, N.Y.

The wood flour or hemicellulose extract used in the present composition and/or method is employed in an amount effective to stabilize the O-halopyridylphosphate insecticide/carrier mixture from thermal degradation. In high concentrate dusts, the wood flour or hemicellulose extract can comprise from about 5 to about 89 percent by weight of the total composition, preferably from about 30 to about 70 percent by weight, more preferably from about 30 to about 50 percent by weight. In low concentrate dusts, the wood flour or hemicellulose extract can comprise from about 90 to about 99.9 percent by weight of the composition, more preferably from about 95 to about 99 percent by weight of the total composition.

The wood flour or hemicellulose extract is usually combined with the O-halopyridylphosphate/carrier admixture in a ratio ranging from about 1 to about 20 parts of the wood flour or hemioellulose extract to 1 part of carrier (weight basis), preferably from about 1 part to about 10 parts of wood flour or hemicellulose extract to 1 part of carrier, and most preferably from about 1.5 to about 4 parts of wood flour or hemicellulose extract to 1 part of carrier.

The compositions of the present invention are usually prepared by uniformly applying the O-halopyridylphosphate insecticide to the desired carrier to give the requisite insecticidal concentration in the compositions. Generally, the O-halopyridylphosphate insecticide is sprayed onto the carrier, and the mixture agitated in a mixer until the insecticide is uniformly absorbed onto the carrier and the wood flour or hemicellulose extract is then added to this mixture. The mixture is then usually ground to a particle size ranging from about 50 microns to about 2400 microns, preferably about 50 microns. The wood flour or hemicellulose extract can also be added to previously ground insecticide-carrier mixtures. The compositions of the present invention can also be prepared by mixing all of the components together, including any wetting agents and/or dispersing agents, which are desired.

In situations where the compositions of the present invention are employed as wettable powders, the compositions can be ground to a even finer particle size, which can range from about 1 to about 30 microns. Wetting agents are added to the finely ground powder to improve its wettability when the powder is added to an aqueous medium. Such wetting agents include but are not limited to alkylnaphthalene sulfonate salts and N-methyl-N-oleoyltaurate salts such as sodium, potassium or ammonium. Dispersing agents can also be combined with the wetting agent to improve the dispersion of the wettable powder when added to an aqueous medium. Typical dispersing agents include the sodium based sulfonates of Kraft lignin and the salts of polymerized alkylnaphthalene sulfonic acids. Typically, the wetting and dispersing agents can comprise between about 3 to about 10 percent (weight basis) of the total insecticidal composition. The wetting and dispersing agents can be combined with the insecticidal compositions on its individual components according to any known methods.

Low concentrate dusts of the present invention can be used in stored grain for protection of barley, oats, rice, sorghum and wheat and the like against injury from stored grain weevils, moths, borers, beetles and mealworms including granary weevil, rice weevil, red flour beetle, confused flour beetle, saw-toothed grain beetle, Indian meal moth, Angoumois grain moth and lesser grain borer. The low concentrate dusts can be applied directly to the grain as it is being loaded or turned into final storage at the rate of from about 10 pounds to about 50 pounds of the dust per 1000 bushels, preferably about 10 pounds of the dust per 1000 bushels. To protect stored grains from attack by Indian meal moth, the dust can be applied to the surface of clean or infested grain at the rate of about 7 pounds per 1000 square feet of grain surface area. The dusts should be applied to the grain as evenly as possible, by any suitable means, such as by sprinkling, blowing, laying, and the like.

The low concentrate dusts can also be applied to the grain while it is in a truck or wagon prior to binning. The requisite amount of the low concentrate dust (10–50 pounds per 1000 bushels) is spread evenly over the surface of the grain in the truck or wagon. The dust can be cut into the grain with any suitable utensil, such as a shovel.

High concentrate dusts (10 to about 90 percent by weight insecticide) can be admixed with additional carrier to prepare the low concentrate dusts as discussed hereinabove.

The compositions of the present invention can also be contacted with plants or plant parts in order to control insects such as crickets or grasshoppers. Such plants typically include vegetables such as tomatoes, cabbage, broccoli, lettuce or watermelons or field crops such as corn, soybeans, cotton, potatoes, wheat or rice. The composition of the present invention can also be applied to non-crop plants in areas such as railroad right-of-ways. Sticker agents, which help the compositions to adhere more tightly to the grain or plant parts, can also be added to the present compositions. Such sticker agents include but are not limited to paraffinic oils, mineral oils such as white mineral oils, free and combined fatty acids, alkylarylpoly-ethoxyethanol, glycol ethers and di-alkylbenzene dicarboxylates.

Typically, the sticker agents can comprise between about 3 to about 10 percent of the total insecticidal composition. Such sticker agents can be combined with the insecticidal composition according to known methods.

The compositions of the present invention can also be employed in non-plant areas such as households and industrial buildings including but not limited to restaurants, apartments, office buildings, warehouses, factories and the like.

The following examples illustrate the present invention and the manner by which it can be practiced but, as such, should not be construed as limitations upon the overall scope of the same.

Example 1 Thermal Stability of Chlorpyrifos-methyl in Low Concentrate Dusts

A predetermined amount of a liquid insecticidal concentrate containing 45.0 percent (weight basis) chlorpyrifos-methyl and 55 percent aromatic solvent and other inerts was sprayed onto a predetermined amount of various selected solid carriers to give prepared mixtures calculated to contain less than 4 percent chlorpyrifos-methyl. The mixture was agitated in a rotating drum to ensure complete and even coverage of the chlorpyrifos-methyl onto the carrier. The mixtures were then ground in a hammermill without a screen to further ensure evenness of carrier coverage. The various ground mixtures were placed in bottles and stored at 50° C. for a period of 0, 14 30 and 60 days. The percentage of chlorpyrifos-methyl remaining in each mixture, after each time period, is set forth below in Table 1.

TABLE 1

Thermal Stability of Chlorpyrifos-methyl stored at 50° C. (122° F.) in Low Concentrate Dusts Containing Less than 4 percent Chlorpyrifos-methyl

| Carrier | Chlorpyrifos-methyl and Solvent as Percent of Formulation | Chlorpyrifos-Methyl as Percent of Formulation (0 Day) | Percent Chlorpyrifos-methyl Remaining | | |
|---|---|---|---|---|---|
| | | | 14 Days | 30 Days | 60 Days |
| Softwood Flour | 5.0 | 3.49 | >100 | 96 | 88 |
| Hemicellulose Extract (Dried) | 5.0 | 3.14 | 97 | 99 | 90 |
| Corn Flour | 5.0 | 3.04 | 94 | 89 | 78 |
| Kaolinite Clay | 5.0 | 2.60 | 18 | 8 | 4 |
| Diatomaceous Earth | 5.0 | 3.01 | 26 | 6 | 0.9 |
| Corn Flour (75%) + Kaolinite Clay (20%) | 5.0 | 2.74 | 91 | 85 | 69 |
| Corn Flour (75%) + Diatomaceous Earth (20%) | 5.0 | 3.11 | 81 | 66 | 45 |
| Corn Flour (20%) + Softwood Flour (75%) | 5.0 | 3.29 | >100 | 92 | 87 |
| Corn Flour (20%) + Hemicellulose Extract (75%) | 5.0 | 3.06 | 99 | 98 | 92 |
| Diatomaceous Earth (20%) + Softwood Flour (75%) | 5.0 | 3.52 | 99 | 90 | 81 |
| Diatomaceous Earth (20%) + Hemicellulose Extract (75%) | 5.0 | 3.01 | 90 | 85 | 71 |
| Kaolinite Clay (75%) + Softwood Flour (20%) | 5.0 | 3.24 | >100 | 89 | 84 |
| Kaolinite Clay (20%) + Hemicellulose Extract (75%) | 5.0 | 3.06 | 90 | 80 | 69 |
| Corn Flour (20%) + Kaolinite Clay (20%) + Softwood Flour (55%) | 5.0 | 3.40 | >100 | 92 | 89 |
| Corn Flour (20%) + Diatomaceous Earth (20%) + Softwood Flour (55%) | 5.0 | 3.35 | 100 | 89 | 83 |

What is claimed is:

1. A composition comprising:
   (a) an insecticidally-effective amount of an O-halopyridylphosphate insecticide of the formula:

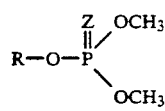

wherein R represents halopyridyl and Z represents oxygen or sulfur, in admixture with
   (b) an inert carrier which is a corn flour or a mineral clay from the group consisting of diatomaceous earth and kaolinite clays, or a mixture of said carriers and
   (c) an amount of an inert stabilizing material effective to thermally stabilize the insecticide-carrier mixture, said stabilizing material is a wood flour or a hemicellulose extract or a mixture thereof.

2. The composition of claim 1 wherein the concentration of O-halopyridylphosphate insecticide in the composition is in the range from about 0.1 to about 95 percent by weight.

3. The composition of claim 2 wherein the O-halopyridylphosphate insecticide is chlorpyrifos-methyl.

4. The composition of claim 2 wherein the carrier comprises about 5 to about 99.9 percent by weight of the total composition.

5. The composition of claim 4 wherein the carrier is a corn flour.

6. The composition of claim 4 wherein the mineral clay is a diatomaceous earth or a kaolinite clay.

7. The composition of claim 4 wherein the stabilizing material is a softwood flour.

8. The composition of claim 4 wherein the stabilizing material is a hemicellulose extract.

9. The composition of claim 4 wherein the carrier is a mixture of a diatomaceous earth and a corn flour.

10. The composition of claim 4 wherein the carrier is a mixture of a corn flour and a kaolinite clay.

11. The composition of claim 4 further comprising an effective amount of a wetting agent, a dispersing agent, a sticker agent or a mixture thereof.

12. A method for protecting stored grain or plants from insect damage comprising applying to the grain or the locus of the plants a composition comprising:
   (a) an insecticidally-effective amount of an O-halopyridylphosphate insecticide of the formula:

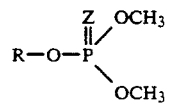

wherein R represents halopyridyl and Z represents oxygen or sulfur, in admixture with (b) an inert carrier which is a corn flour or a mineral clay from the group consisting of diatomaceous earth and kaolinite clays, or a mixture of said carriers and (c) an amount of an inert stabilizing material effective to thermally stabilize the insecticide-carrier mixture, said stabilizing material is a wood flour or a hemicellulose extract or a mixture thereof.

13. The method of claim 12 wherein the concentration of the O-halopyridylphosphate insecticide in the composition is in the range from about 0.1 percent to about 95 percent by weight.

14. The method of claim 13 wherein the O-halopyridylphosphate insecticide is chlorpyrifos-methyl.

15. The method of claim 13 wherein the carrier comprises about 5 to about 99.9 percent by weight of the total composition.

16. The method of claim 15 wherein the carrier is a corn flour.

17. The method of claim 15 wherein the mineral clay is a diatomaceous earth or a kaolinite clay.

18. The method of claim 15 wherein the stabilizing material is a softwood flour.

19. The method of claim 15 wherein the stabilizing material is a hemicellulose extract.

20. The method of claim 15 wherein the carrier is a mixture of a corn flour and a diatomaceous earth.

21. The method of claim 15 wherein the carrier is a mixture of a corn flour and a kaolinite clay.

22. The method of claim 13 wherein the composition further contains an effective amount of a wetting agent, a dispersing agent, a sticker agent or a mixture thereof.

* * * * *